STRAWBERRY PLANT

Filed Nov. 14, 1973

United States Patent

Plant Pat. 3,713
Patented May 6, 1975

3,713
STRAWBERRY PLANT

Herschel L. Boll, R.R. 4, Champaign, Ill. 61820

Filed Nov. 14, 1973, Ser. No. 415,496
Int. Cl. A01h *5/03*
U.S. Cl. Plt.—49 1 Claim My invention relates to a new and distinct variety of strawberry plant. It was discovered by me as a mutation of Armore on my farm at Champaign, Ill., in 1959.

In the spring of 1959, a row of plants was planted from a clone of true-to-name Armore (a June-bearing variety), which I had, and had observed for about 9 years. Several weeks later I discovered that a plant that was planted in this new row was everbearing.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. The only noticeable differences between my new variety and Armore (except the everbearing characteristic) are that it produces less runners, and the flesh of its fruit is darker red, is slightly tart instead of sweet, and has less flavor. My new variety has proved itself to have unusual possibilities because of its everbearing habit of growth; its high productivity; its vigorous growth; its continuous bearing of fruit from June until freezing weather; its runners usually producing flower buds before roots; and its medium red, glossy, very firm, evenly colored, and very attractive fruit.

Figure 1:
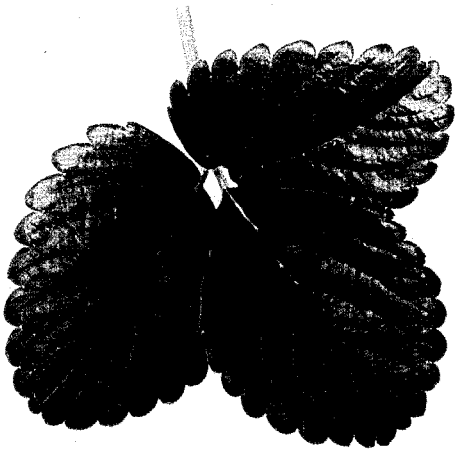
FIG. 1 shows a typical leaf in full color.
Figure 2:
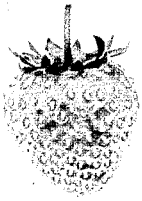
FIG. 2 is a berry of typical shape.
Figure 3:
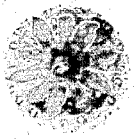
FIG. 3 shows a typical top view of a berry, exhibiting the small to medium-sized calyx.
Figure 4:
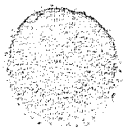
FIG. 4 illustrates a typical central cross-section of a berry.

In general, the distinct and new variety of strawberry plant, which is the subject of my invention and discovery, is characterized by its everbearing habit of growth; by its high productivity; by its vigorous growth; by its continuous bearing of fruit from June until freezing weather; by its runners usually producing flower buds before roots; and by its medium red, glossy, very firm, evenly colored, and very attractive fruit. These characteristics I now refer to in greater detail. Color plate references are according to Color Standards and Color Nomenclature by Robert Ridgway.

Under the conditions at Champaign, Ill., my new variety of plant is everbearing and high in productivity, largely because it bears continuously from June until freezing weather. It appears to be adapted farther south in the Midwest than any other everbearer. It is even better adapted in southwestern Michigan. The plants are vigorous, and are medium in height. In general, they produce few runners, less than Locke Lake Ruby (Plant Pat. 2,429), Sonjana (Plant Pat. 1,691), or Gem; however, some plants produce many, while other produce none. Usually flower buds appear on the runners before the roots appear.

The leaves are medium green in color, or are approximately Forest Green (Plate XVII), or varying from Varley's Green (Plate XVIII) to Forest Green (Plate XVII) to Cerro Green (Plate V), depending mainly on soil fertility, but also depending on other soil conditions, exposure, and weather and climatic conditions. The leaves are medium in size, slightly glossy to glossy, slightly cupped, and medium in rugosity. The flowers are perfect. The date of the fruit blossoms in 1972 at Champaign, Ill., was May 5.

At Champaign, Ill., my new variety of strawberry plant begins to mature its fruit in midseason (at about the same time as Catskill, but Catskill is a June-bearer), and bears continuously until freezing weather. The berries are well formed throughout the bearing season.

The fruit is medium red (it is medium dark red for Locke Lake Ruby), or is approximately Nepal Red (Plate I), or varying from Jasper Red (Plate XIII) to Nepal Red (Plate I) to Carmine Red (Plate I), depending mainly on exposure, but also depending on soil, weather, and climatic conditions. The fruit is medium to large. It is small to medium in size for Gem. The fruit of my new variety is conic in shape, while it is heart-shaped for Locke Lake Ruby, blunt conic for Sonjana, and short wedge to oblate for Gem. It is glossy, very firm, evenly colored, and very attractive in appearance. The pedicels are long and slender.

The calyx is small to medium in size. The achenes are raised (they protrude very slightly for Locke Lake Ruby, and are indented for Sonjana), and are yellow to red depending on exposure.

Under the conditions existing where I have reproduced and tested my new variety of strawberry plant, the flesh of the berry is medium light red to medium red (it is red with a whitish area for Locke Lake Ruby, and whitish for Sonjana), or is approximately Jasper Red (Plate XIII), or varying from Strawberry Pink (Plate I) to Jasper Red (Plate XIII) to Nepal Red (Plate I), depending mainly on exposure, but also depending on soil, weather, and climatic conditions. The flesh is firm. The fruit is slightly tart (it is acid for Gem), and is medium in flavor.

The strawberry above described, and the plant producing it, of course, may vary in slight details, depending on soil, weather, and climatic conditions.

What I claim is:

1. A new and distinct variety of strawberry plant substantially as herein shown and described, characterized by its everbearing habit of growth; by its high productivity; by its vigorous growth; by its continuous bearing of fruit from June until freezing weather; by its runners usually producing flower buds before roots; and by its medium red, glossy, very firm, evenly colored, and very attractive fruit.

References Cited

UNITED STATES PATENTS

| | | | |
|---|---|---|---|
| P.P. 1,691 | 3/1958 | Hummel | Plants—49 |
| P.P. 2,429 | 7/1964 | Brunnen | Plants—49 |

ROBERT E. BAGWILL, Primary Examiner